US010010300B2

(12) United States Patent
Yao

(10) Patent No.: US 10,010,300 B2
(45) Date of Patent: Jul. 3, 2018

(54) BITE-BLOCK AND FILM-HOLDING DEVICE

(71) Applicant: DENSMART DENTAL CO., LTD., Taoyuan (TW)

(72) Inventor: Yin Chao Yao, Taoyuan (TW)

( * ) Notice: Subject to any disclaimer, the term of this patent is extended or adjusted under 35 U.S.C. 154(b) by 206 days.

(21) Appl. No.: 15/180,745

(22) Filed: Jun. 13, 2016

(65) Prior Publication Data

US 2017/0065236 A1 Mar. 9, 2017

(30) Foreign Application Priority Data

Aug. 12, 2015 (TW) .............................. 104213029 U

(51) Int. Cl.
*A61B 6/14* (2006.01)
*A61B 6/00* (2006.01)

(52) U.S. Cl.
CPC .............. *A61B 6/145* (2013.01); *A61B 6/587* (2013.01)

(58) Field of Classification Search
None
See application file for complete search history.

(56) References Cited

U.S. PATENT DOCUMENTS

| | | | | |
|---|---|---|---|---|
| 4,554,676 A * | 11/1985 | Maldonado | .......... | G03B 42/042 378/147 |
| 4,815,117 A * | 3/1989 | Waldo | .................. | G03B 42/042 378/168 |
| 4,965,885 A * | 10/1990 | Fuhrmann | ............ | G03B 42/042 378/168 |
| 5,327,477 A * | 7/1994 | Levy | ....................... | A61B 6/145 378/168 |
| 6,033,111 A * | 3/2000 | Winters | ................ | G03B 42/042 378/168 |
| 6,382,831 B1 * | 5/2002 | Bacchetta | ............ | G03B 42/042 378/167 |
| 2013/0089185 A1 * | 4/2013 | Winters | .................. | A61B 6/145 378/170 |
| 2015/0230764 A1 * | 8/2015 | Charnegie | .............. | A61B 6/145 378/145 |

* cited by examiner

*Primary Examiner* — Hoon Song

(57) ABSTRACT

A bite-block and film-holding device is used with an x-ray film or a digital image sensor and held by a patient between teeth to align with an external camera device for dental radiographic imaging of the patient's teeth. The bite-block and film-holding device includes a disposable film holder having a bite block portion, a film-holding portion made of a plastic material, and a bonding member having a release layer attached thereto; and an aiming assembly having a coupling arm coupled to the disposable film-holder and an aiming ring assembly installed on the camera device and connected to the coupling arm. The aiming ring assembly is adjustable in position for the camera device to face at a right angle to the film-holding portion. After the dental radiographic imaging, the disposable film holder is separated from the aiming assembly and discarded to ensure the patient's oral cavity hygiene and health.

11 Claims, 17 Drawing Sheets

BITE-BLOCK AND FILM-HOLDING DEVICE

FIELD OF THE INVENTION

The present invention relates to a bite-block and film-holding device that facilitates dental radiographic imaging; and more particularly to a bite-block and film-holding device that is simple in structure and includes a film-holding portion, which is in contact with a patient's oral cavity and can be removed from the device and discarded alone after the dental radiographic imaging.

BACKGROUND OF THE INVENTION

Dental healthcare has close relation with people's eating hygiene and good living quality of senior years. The advancement of healthcare industry and many hygiene and health-related promotion campaigns have drawn people's attention to dental healthcare. While teeth cleaning with a toothbrush, dental floss or inter-dental brushes provides preventive effect on dental problems, regular oral cavity examinations can follow up any change in dental structures to discover oral cavity-related problems as early as possible. Further, correction of malpositioned teeth or jaws can improve a person's facial appearance, and people having even white teeth give others better impression of them. Most people can get convenient dental examinations at small-scaled dental clinics everywhere.

To have a clear idea about a patient's existing dental structure, a dentist at the dental clinic would usually use oral and dental imaging equipment to capture images of the patient's all or some specific teeth, and evaluates the patient's teeth condition based on the captured dental images to facilitate an accurate decision for subsequent dental surgery or correction. The oral and dental imaging equipment includes two main types, a first one of which requires the positioning of a small piece of x-ray film in the patient's oral cavity to help dental radiographic imaging. The other type of oral and dental imaging equipment does not require an x-ray film. The widely available x-ray films can be divided into two major types, namely, a physical x-ray film and a digital image sensor. In the process of dental radiographic imaging, the physical x-ray film is positioned in the patient's oral cavity and might cause discomfort to the patient or form a risk to the patient's dental hygiene. On the other hand, the dental clinics have to purchase x-ray films that match the model and brand of the oral and dental imaging equipment they currently use. In the event the purchased x-ray films are wrong in size or specifications and could not be used with the existing oral and dental imaging equipment, a lot of money will be wasted.

SUMMARY OF THE INVENTION

A primary object of the present invention is to provide a simple and low-cost bite-block and film-holding device for dental radiographic imaging, of which a partial structure that is in contact with a patient's oral cavity during the dental radiographic imaging can be removed and discarded after completion of the dental radiographic imaging to meet the requirement for patient's oral cavity hygiene and health.

Another object of the present invention is to provide a bite-block and film-holding device that includes an aiming assembly, which is located outside the patient's oral cavity and can be adjusted in position during the dental radiographic imaging. With the aiming assembly, a camera device connected thereto can be accurately aligned with the patient's teeth that are to be x-ray imaged. Therefore, the dental radiographic imaging can be completed with increased accuracy and shortened time to avoid unnecessary waste of valuable medical materials.

A further object of the present invention is to provide a bite-block and film-holding device that includes a bonding member for detachably adhering an x-ray film or a digital image sensor to a disposable film holder of the device. After completion of the dental radiographic imaging, the x-ray film or the digital image sensor can be removed from the disposable film holder and be disinfected for reuse, and can therefore be used more times and have longer service life.

A still further object of the present invention is to provide a bite-block and film-holding device that includes a disposable film holder, which is configured for use with differently sized x-ray films or digital image sensors for dental radiographic imaging. The disposable film holder has a bonding member attached thereto for adhering the x-ray film or the digital image sensor to a specific area on the disposable film holder. Therefore, the disposable film holder can be used to hold x-ray films or digital image sensors of different brands and different sizes.

To achieve the above and other objects, the bite-block and film-holding device according to the present invention is used with an x-ray film or a digital image sensor, and is held by a patient between teeth to align with an external camera device for dental radiographic imaging of the patient's teeth. The bite-block and film-holding device according to the present invention includes a disposable film holder and an aiming assembly. The disposable film holder includes a bite block portion having two bite surfaces respectively extended in an X-Y plane; a film-holding portion made of a plastic material and connected to an end of the bite block portion, and having a holding surface extended in a Y-Z plane; and a bonding member having two bonding surfaces provided on two opposite sides thereof. One of the bonding surfaces is adhered to the holding surface of the film-holding portion while the other bonding surface is used to adhesively hold the x-ray film or the digital image sensor thereto.

The aiming assembly includes a coupling arm having an end coupled to the disposable film holder; and an aiming ring assembly installed on the camera device and connected to another end of the coupling arm. The aiming ring assembly is adjustable in position for the camera device to face at a right angle to the holding surface of the film-holding portion.

After completion of the dental radiographic imaging of the patient's teeth, the disposable film holder is separated from the aiming assembly and another new one is coupled to the aiming assembly for use in the dental radiographic imaging of another patient.

In a preferred embodiment of the present invention, the bite block portion is formed of one single bite member, of which an upper and a lower side form an upper bite surface and lower bite surface, respectively.

In a preferred embodiment of the present invention, the film-holding portion is formed of one single film-holding member. The film-holding member includes an upper part and a lower part, which are extended upward and downward in the Y-Z plane relative to the bite block portion. The upper part is located corresponding to the patient's upper teeth, and the lower part is located corresponding to the patient's lower teeth.

The plastic material for making the film-holding portion is selected from the group consisting of polycarbonate (PC), polyethylene (PE), polyvinyl chloride (PVC), polypropylene (PP), and acrylonitrile butadiene styrene (ABS).

In a preferred embodiment of the present invention, the bonding member further includes a release layer attached to one of the bonding surfaces that is to be adhered to the x-ray film or the digital image sensor.

In a preferred embodiment of the present invention, the aiming ring assembly includes a sub-coupling arm connected at an end to the coupling arm and an aiming ring connected to another opposite end of the sub-coupling arm.

The coupling arm and the sub-coupling arm are respectively configured as a shaft and a sleeve, and the shaft can be correspondingly fitted in the sleeve. Further, the coupling arm is connected to one of the bite block portion and the film-holding portion via a coupling structure. When the dental radiographic imaging for one patient is completed, the shaft having been in contact with the patient's oral cavity or lips can be removed from the sleeve of the aiming ring assembly and discarded along with the disposable film holder.

In a preferred embodiment of the present invention, the disposable film holder further includes an alignment portion for ensuring accurate attachment of the x-ray film or the digital image sensor to the film-holding portion. The alignment portion is connected to the holding surface of the film-holding portion to provide a supporting surface extended in an X-Y plane; and the x-ray film or the digital image sensor is adhered to the film-holding portion with an edge in contact with the supporting surface.

In a preferred embodiment of the present invention, the alignment portion is formed of one single alignment member. The alignment member extends from the holding surface of the film-holding portion in an X-Y plane; and the bite block portion and the alignment portion are located at two opposite sides of the film-holding portion.

In an operable embodiment of the present invention, the coupling structure is configured as an insert-to-connect structure, which includes an insertion hole provided on one of the bite block portion, the film-holding portion and the alignment portion and an insertion rod provided on the coupling arm for correspondingly inserting into the insertion hole.

In another operable embodiment of the present invention, the coupling structure is configured as a snap-fit structure, which includes a plurality of sunken holes provided on one of the bite block portion, the film-holding portion and the alignment portion at a surface that correspondingly contacts with the coupling arm, and a plurality of bosses provided on the coupling arm at a surface that correspondingly contacts with one of the bite block portion, the film-holding portion and the alignment portion.

In still another operable embodiment, the coupling structure is configured as an interference-fit structure, which includes a rod extended from an end of the coupling arm and a groove formed on one of the bite block portion and the alignment portion for correspondingly receiving the rod therein; and the rod fitted in the groove is coplanar with the bite block portion or the alignment portion.

With the above arrangements, the bite-block and film-holding device of the present invention is characterized in that some structures thereof, including a film holder and a coupling arm, are disposable. The disposable structures are disposed in the patient's oral cavity during the process of dental radiographic imaging and will have the patient's saliva and other oral cavity tissues attached thereto. After the dental radiographic imaging is completed, the x-ray film or the digital image sensor is removed from the bite-block and film-holding device and can be disinfected for reuse while the disposable structures having the patient's saliva and other oral cavity tissues attached thereto are separated from other portions of the bite-block and film-holding device and discarded. With this structural design, it is able to eliminate the patient's concern about the sanitation and safety of the bite-block and film-holding device for dental radiographic imaging.

The film-holding portion or the entire disposable film holder or the whole bite-block and film-holding device of the present invention, which is exposed to x-ray in the process of dental radiographic imaging, is made of a plastic material. And, with the bonding member for adhering the x-ray film or the digital image sensor to the film-holding portion, the bite-block and film-holding device of the present invention can be used with x-ray films or digital image sensors of different sizes and specifications.

The bite-block and film-holding device of the present invention is also characterized in including an aiming assembly, which is located corresponding to the disposable film holder in the process of dental radiographic imaging. The disposable film holder along with the x-ray film or the digital image sensor adhered thereto are located inside the patient's oral cavity, while the aiming assembly is located outside the patient's oral cavity. Via the aiming assembly located outside the patient's oral cavity, the camera device for dental radiographic imaging can be accurately aligned with the patient's teeth that require radiographic imaging.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
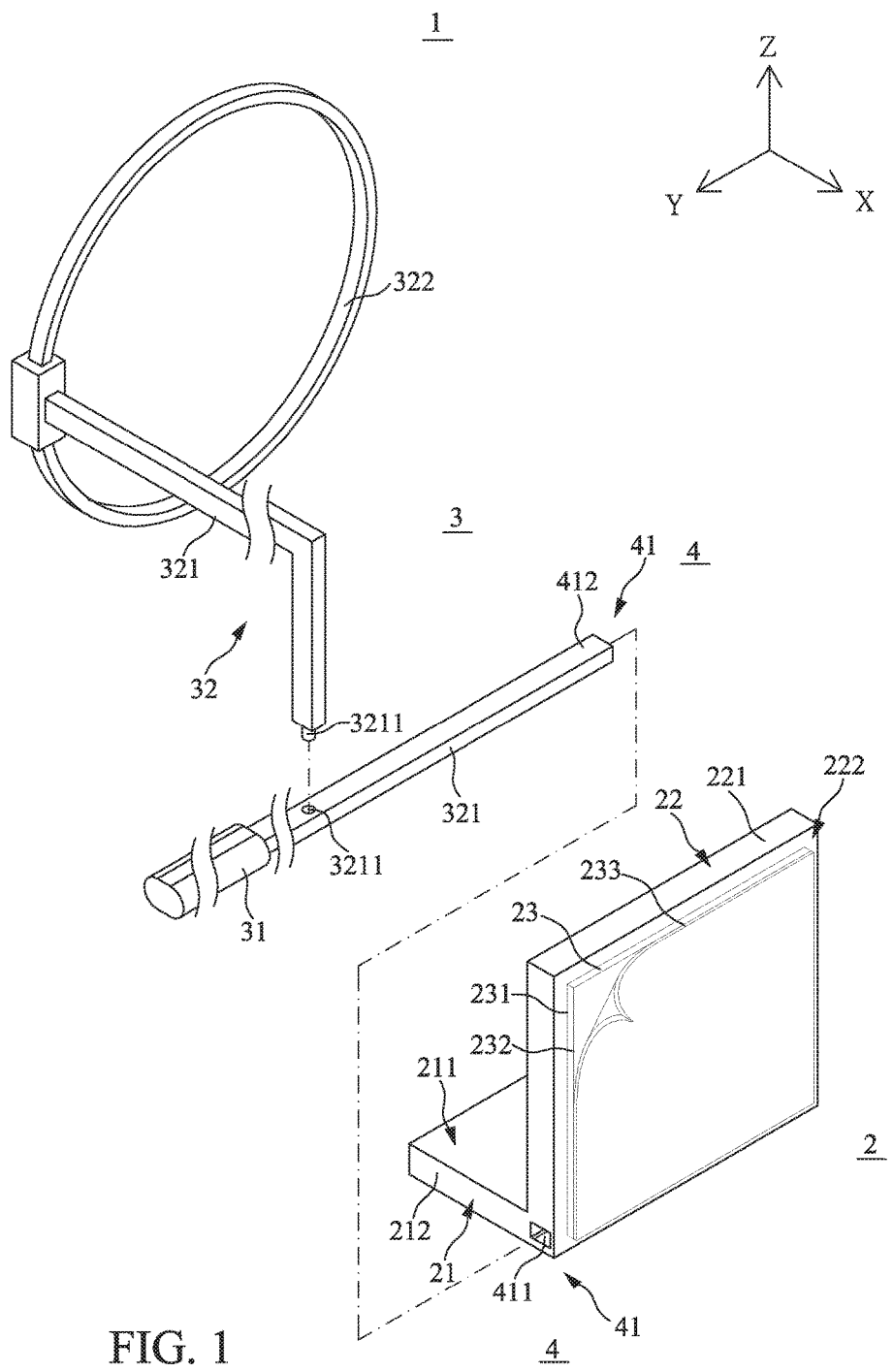
FIG. 1 is an exploded perspective view of a bite-block and film-holding device according to a first preferred embodiment of the present invention, showing a first type of aiming ring assembly and an insert-to-connect structure thereof.

The present invention will now be described with some preferred embodiments thereof and by referring to the accompanying drawings. For the purpose of easy to understand, elements that are the same in the preferred embodiments are denoted by the same reference numerals.

Please refer to FIG. 1. A bite-block and film-holding device 1 according to a first preferred embodiment of the present invention includes a disposable film holder 2 and an aiming assembly 3.

The disposable film holder 2 includes a bite block portion 21, a film-holding portion 22, and a bonding member 23. In the first preferred embodiment, the bite block portion 21 is formed of one single bite member 212 that provides two bite surfaces 211 respectively located in an x-y plane. One of the two bite surfaces 211 located on an upper side of the bite member 212 is defined as an upper bite surface 213, while the other bite surface 211 located on a lower side of the bite member 212 is defined as a lower bite surface 214.

In the first preferred embodiment, the film-holding portion 22 is formed of one single film-holding member 221, which is made of a plastic material selected from the group consisting of polycarbonate (PC), polyethylene (PE), polyvinyl chloride (PVC), polypropylene (PP), and acrylonitrile butadiene styrene (ABS). Alternatively, the entire disposable film holder 2 or the whole bite-block and film-holding device 1 according to the present invention can be completely made of any one of the above-mentioned plastic materials. The film-holding member 221 is extended from an end of the bite block portion 21 in a Y-Z plane to form a holding surface 222. It is noted the bite block portion 21 and the film-holding portion 22 in the first preferred embodiment are integrally formed.

The bonding member 23 can also be made of a plastic material. Two opposite sides of the bonding member 23 respectively form a first bonding surface 231 and a second bonding surface 232. According to a first operable embodiment of the present invention as shown in FIG. 2A, the first bonding surface 231 is adhered to the holding surface 222 of the film-holding portion 22, while the second bonding surface 232 has a release layer 233 attached thereto to protect the bonding member 23 against dust and dirt.

The aiming assembly 3 includes a coupling arm 31, which is coupled to the disposable film holder 2. In the illustrated first preferred embodiment, the aiming assembly 3 further includes an aiming ring assembly 32, which includes a sub-coupling arm 321 for connecting at an end to the coupling arm 31 and an aiming ring 322 connected to another opposite end of the sub-coupling arm 321. The coupling arm 31 is configured as a rod. The sub-coupling arm 321 and the aiming ring 322 are pivotally connected and are therefore movable relative to each other. In the illustrated first preferred embodiment, the aiming ring 322 can be moves back and forth while keeping in parallel with the Y-Z plane. In the first preferred embodiment, the sub-coupling arm 321 is provided with pivotal means 3211, which include an insert and a corresponding insertion hole. With the pivotal means 3211, a dental radiographic imaging assistant can move the aiming ring 322 back and forth relative to the coupling arm 31, so that the aiming ring 322 connected to the sub-coupling arm 321 is adjusted to one lateral side of the coupling arm 31 and parallel to a centerline of the coupling arm 31. The coupling arm 31 is connected to the bite block portion 21 or the film-holding portion 22 via a coupling structure 4, and the aiming ring assembly 32 is installed on a camera device 7 (see FIG. 6) and connected to the coupling arm 31. After completion of the dental radiographic imaging, the disposable film holder 2 is separated from the aiming assembly 3, and the same aiming assembly 3 can be assembled to another new disposable film holder 2 for use in the dental radiographic imaging of another patient. In the illustrated first preferred embodiment, the aiming assembly 3 is integrally formed.

As can be seen in FIG. 1, in the illustrated first preferred embodiment, the coupling structure 4 connects the coupling arm 31 to the film-holding portion 22. The coupling structure 4 in the illustrated first embodiment is configured as an insert-to-connect structure 41, which includes an elongated insertion hole 411 provided on the film-holding portion 22 and an insertion rod 412 for correspondingly inserting into the insertion hole 411 to engage with the film-holding portion 22. With the arrangements of the aiming assembly 3 and the coupling structure 4, the dental radiographic imaging assistant is able to quickly position the disposable film holder 2 in the patient's oral cavity at teeth to be x-ray examined. The dental radiographic imaging assistant and the patient need not to put the disposable film holder 2 into the patient's mouth with fingers, which advantageously avoids bacterial contamination of the patient's oral cavity.

Figure 2A:
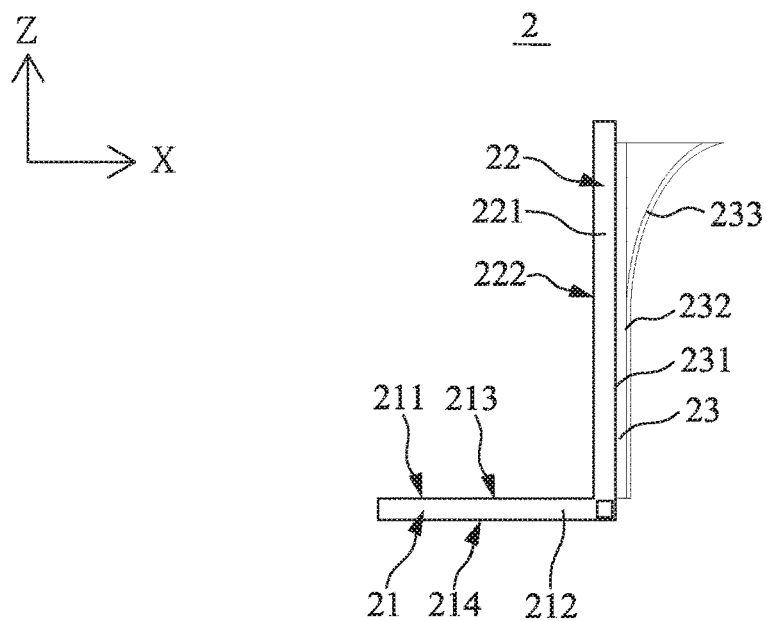
FIG. 2A is a side view showing a film-holding portion of the bite-block and film-holding device of FIG. 1 includes a bonding member that is adhered at a first bonding surface to a holding surface of the film-holding portion.
Figure 2B:
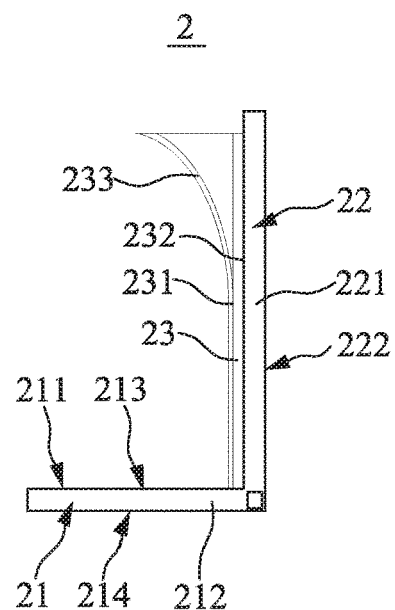
FIG. 2B is a side view showing a film-holding portion of the bite-block and film-holding device of FIG. 1 includes a bonding member that is adhered at a second bonding surface to a holding surface of the film-holding portion.

According to a first operable embodiment of the present invention, the bonding member 23 is adhered at the first bonding surface 231 to the holding surface 222 of the film-holding portion 22, as shown in FIG. 2A. In this case, the patient's teeth and an x-ray film 5 (see FIG. 3) or a digital image sensor 6 (see FIG. 5) attached to the bonding member 23 are located at two opposite sides of the film-holding portion 22. On the other hand, according to a second operable embodiment of the present invention, the bonding member 23 is adhered at the second bonding surface 232 to the holding surface 222 of the film-holding portion 22, as shown in FIG. 2B. In this case, the patient's teeth and the x-ray film 5 or the digital image sensor 6 attached to the bonding member 23 are located at the same side of the holding surface 222 of the film-holding portion 22.

Figure 3:
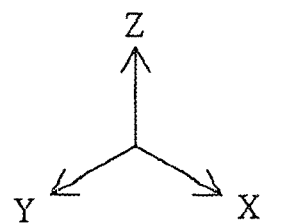
FIG. 3 is a perspective view showing the bonding member of FIG. 2A with an x-ray film attached thereto.
Figure 3:
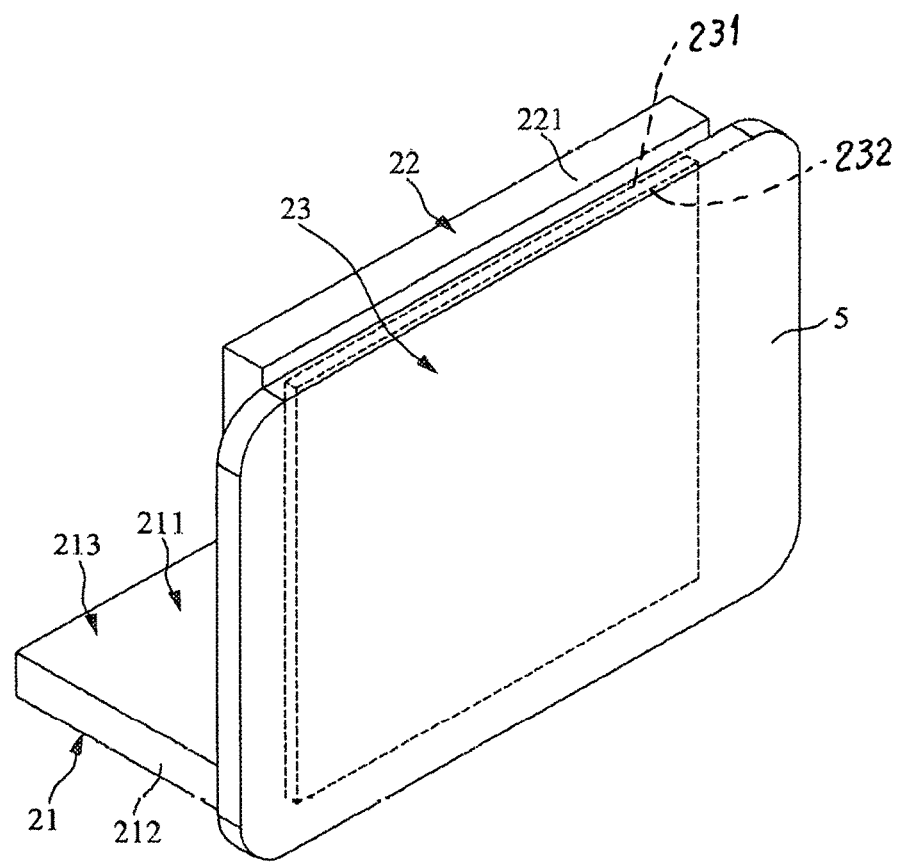

Please refer to FIGS. 2A and 3. During the process of dental radiographic imaging, the disposable film holder 2 can be used with an x-ray film 5 to capture an image of the patient's some teeth. The x-ray film 5 is a very thin x-ray film. After the release layer 233 is peeled off from the bonding member 23, which is adhered at the first bonding surface 231 to the holding surface 222 of the film-holding portion 22, the x-ray film 5 is then adhered to the second bonding surface 232 of the bonding member 23.

Figure 4:
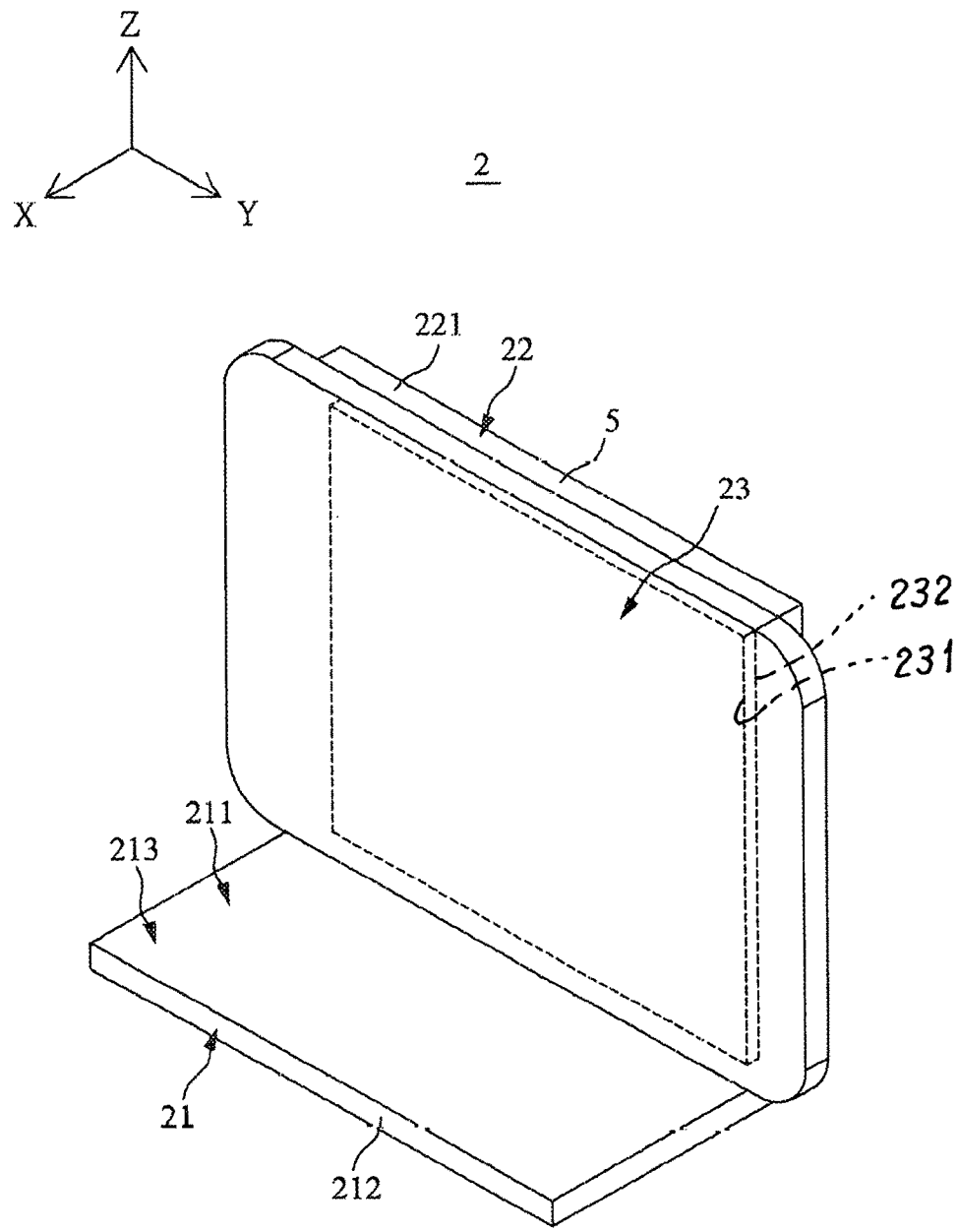
FIG. 4 is a perspective view showing the bonding member of FIG. 2B with an x-ray film attached thereto.

Please refer to FIGS. 2B and 4, in which it is shown the release layer 233 is attached to the first bonding surface 231 of the bonding member 23. After the release layer 233 is peeled off from the bonding member 23, which is adhered at the second bonding surface 232 to the holding surface 222 of the film-holding portion 22, the x-ray film 5 is then adhered to the first bonding surface 231 of the bonding member 23.

Figure 5:
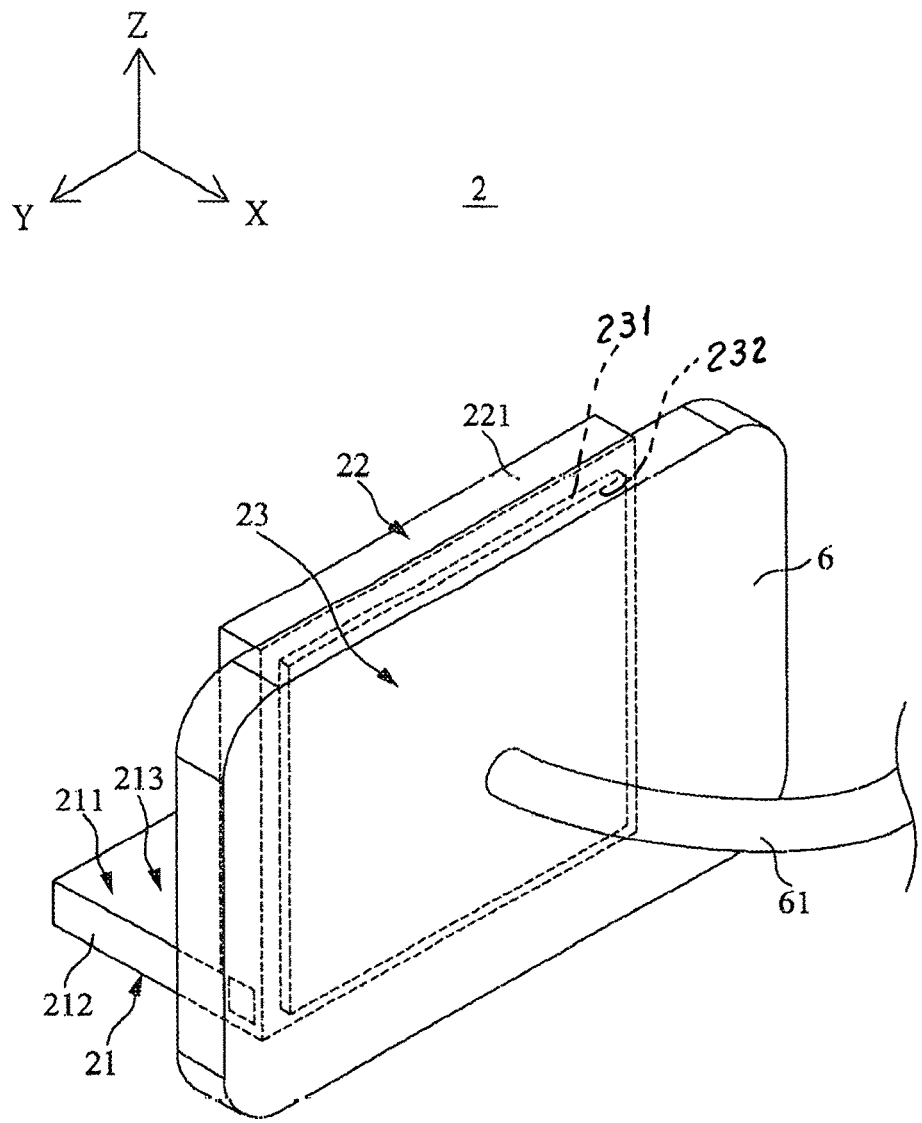
FIG. 5 is a perspective view showing the bonding member of FIG. 2A with a digital image sensor attached thereto.

Referring to FIG. 5. During the process of dental radiographic imaging, the disposable film holder 2 can be used with a digital image sensor 6 to capture an image of the patient's some teeth. The digital image sensor 6 has a specific thickness and volume, and has a transmission cable 61 connected thereto to enable conversion of captured image into digital data for outputting. As can be seen in FIG. 5, the digital image sensor 6 is adhered to the second bonding surface 232 of the bonding member 23.

Figure 6:
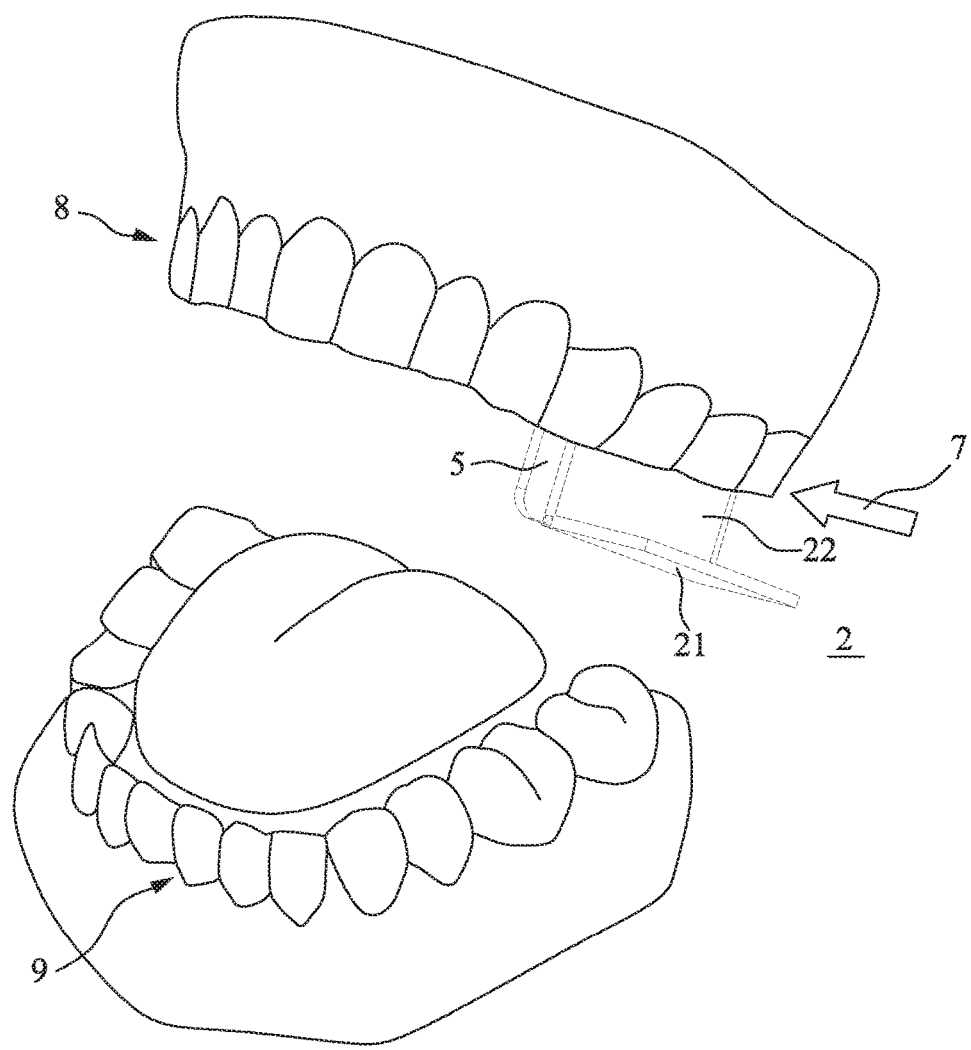
FIG. 6 schematically shows an example of positioning the bite-block and film-holding device of FIG. 1 in a patient's mouth for use.

Please refer to FIG. 6. When the disposable film holder 2 of the bite-block and film-holding device 1 is positioned in the patient's oral cavity, the patient directly bites on the bite block portion 21 with the patient's upper teeth 8 and lower teeth 9 in contact with the upper bite surface 213 and the lower bite surface 214 of the bite block portion 21, respectively. In this example, the bite block portion 21 is facing toward an inner side of the patient's oral cavity, and the x-ray film 5 or the digital image sensor 6 adhered to the bonding member 23 and the patient's teeth to be x-ray imaged are located at two opposite sides of the film-holding portion 22. Thereafter, adjust the aiming ring assembly 32 for the camera device 7 to face at a right angle to the holding surface 222 of the film-holding portion 22. The camera device 7 emits x-ray radiation and the x-ray film 5 or the digital image sensor 6 is correspondingly irradiated to complete the dental radiographic imaging of the patient's teeth.

Figure 7:
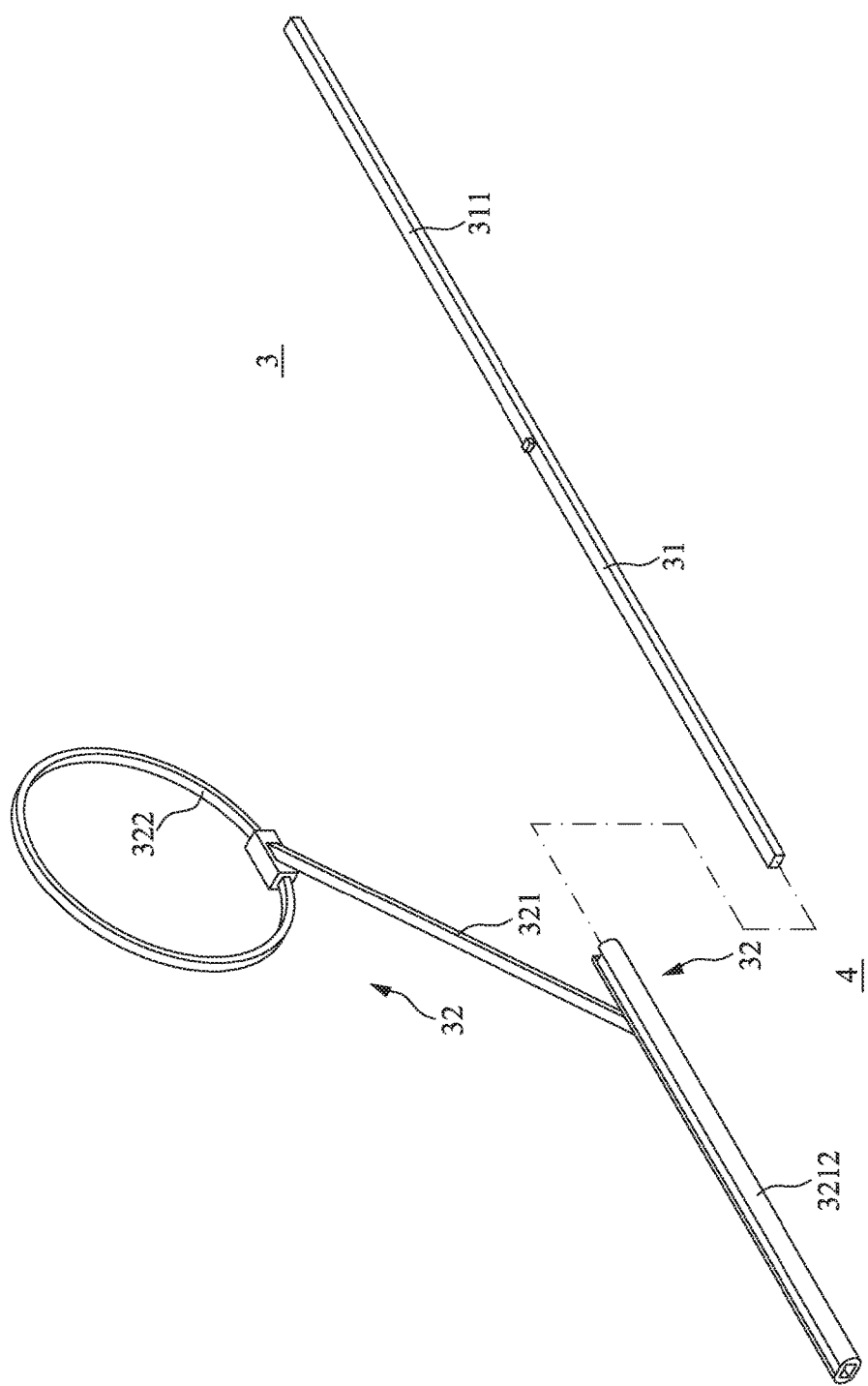
FIG. 7 is an exploded perspective view of a second type of aiming ring assembly for the bite-block and film-holding device of the present invention.

FIG. 7 shows a second type of aiming ring assembly 32 for the bite-block and film-holding device 1 of the present invention. In FIG. 1, the first type of aiming ring assembly 32 of the aiming assembly 3 includes a sub-coupling arm 321 connected at an end to the coupling arm 31 and an aiming ring 322 connected to another opposite end of the sub-coupling arm 321. In the second type of aiming ring assembly 32 as shown in FIG. 7, the sub-coupling arm 321 and the aiming ring 322 are pivotally turnably connected to each other, allowing the aiming ring 322 to be moved back and forth while keeping in parallel with the x-y plane. Further, according to the second type of aiming ring assembly 32, the coupling arm 31 and the sub-coupling arm 321 are respectively configured as a shaft 311 and a sleeve 3212. The shaft 311 can be correspondingly fitted in the sleeve 3212 and freely removed therefrom. With this arrangement, when the dental radiographic imaging for one patient is completed, the shaft 311 having been in contact with the patient's oral cavity can be removed from the sleeve 3212 of the aiming ring assembly 32 and discarded along with the disposable film holder 2.

Figure 8A:
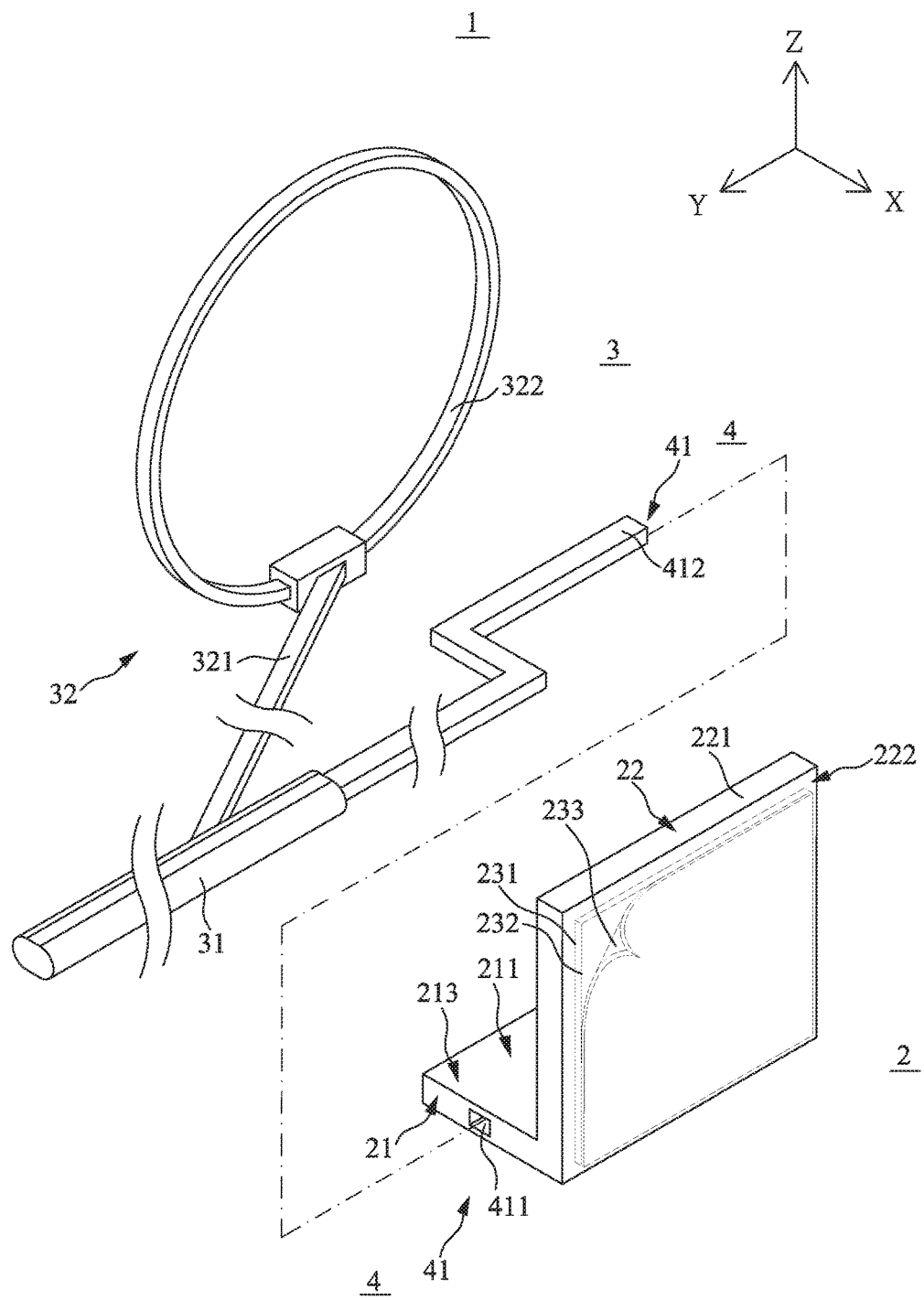
FIG. 8A is an exploded perspective view of a bite-block and film-holding device according to a second preferred embodiment of the present invention, showing an insert-to-connect structure thereof.
Figure 8B:
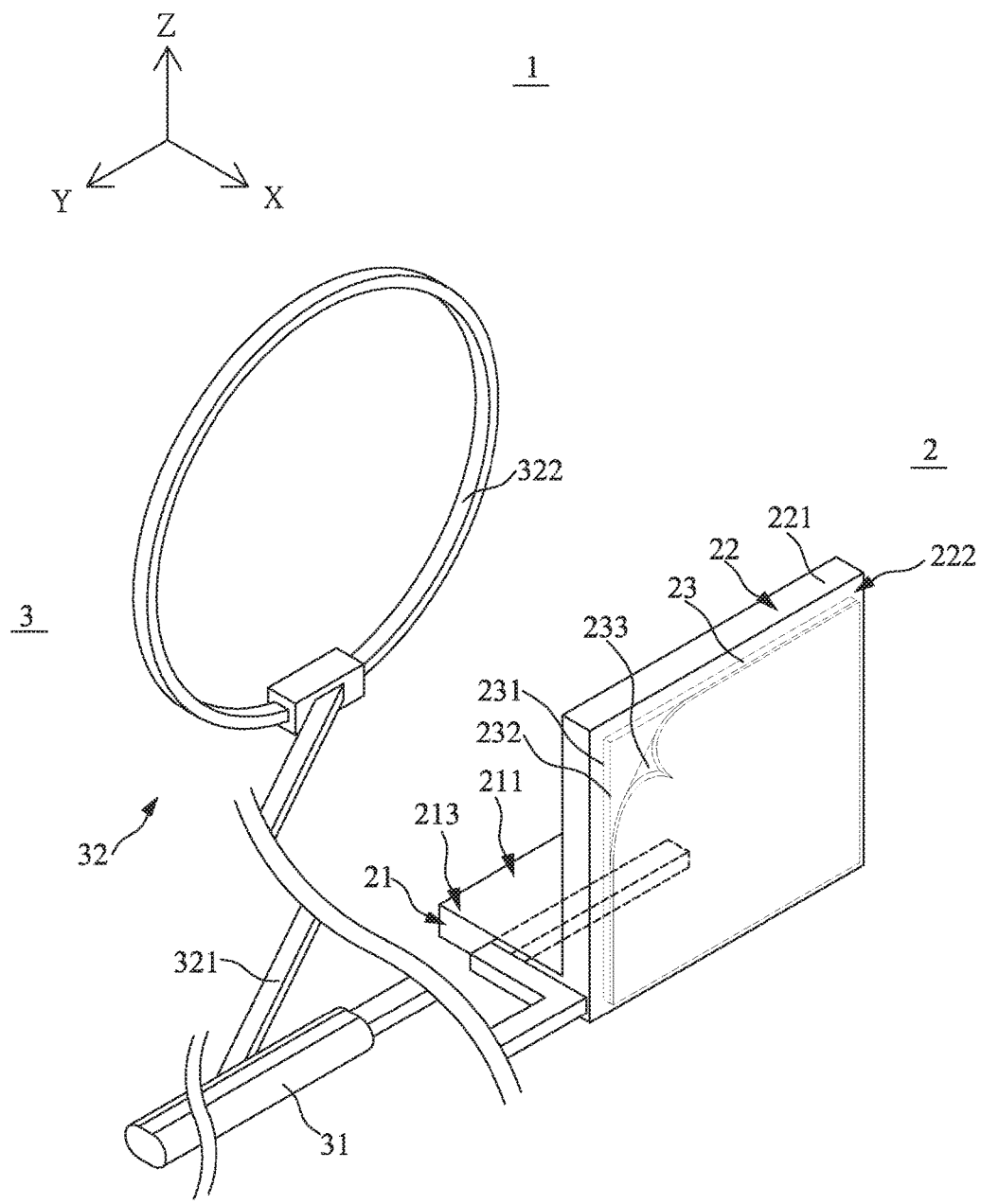
FIG. 8B is an assembled view of FIG. 8A.

FIGS. 8A and 8B are exploded and assembled perspective views, respectively, of a bite-block and film-holding device 1 according to a second preferred embodiment of the present invention. The second preferred embodiment is different from the first one in that the coupling structure 4 thereof connects the coupling arm 31 to the bite block portion 21. In the illustrated second preferred embodiment, the coupling structure 4 is configured as an insert-to-connect structure 41, which includes an elongated insertion hole 411 provided on the bite block portion 21 and an insertion rod 412 for correspondingly inserting into the insertion hole 411 to engage with the bite block portion 21. Further, in the second preferred embodiment, the coupling arm 31 is configured as a bent bar. When a front end of the coupling arm 31, i.e. the insertion rod 412, is inserted into the insertion hole 411, a bent section of the coupling arm 31 that is immediately located outside the bite block portion 21 now fitly bears against one side of the bite block portion 21 to locate in the same X-Y plane as the bite block portion 21. Since the second preferred embodiment is similar to the first one in all other structural features, it is not repeatedly described herein.

Figure 9:
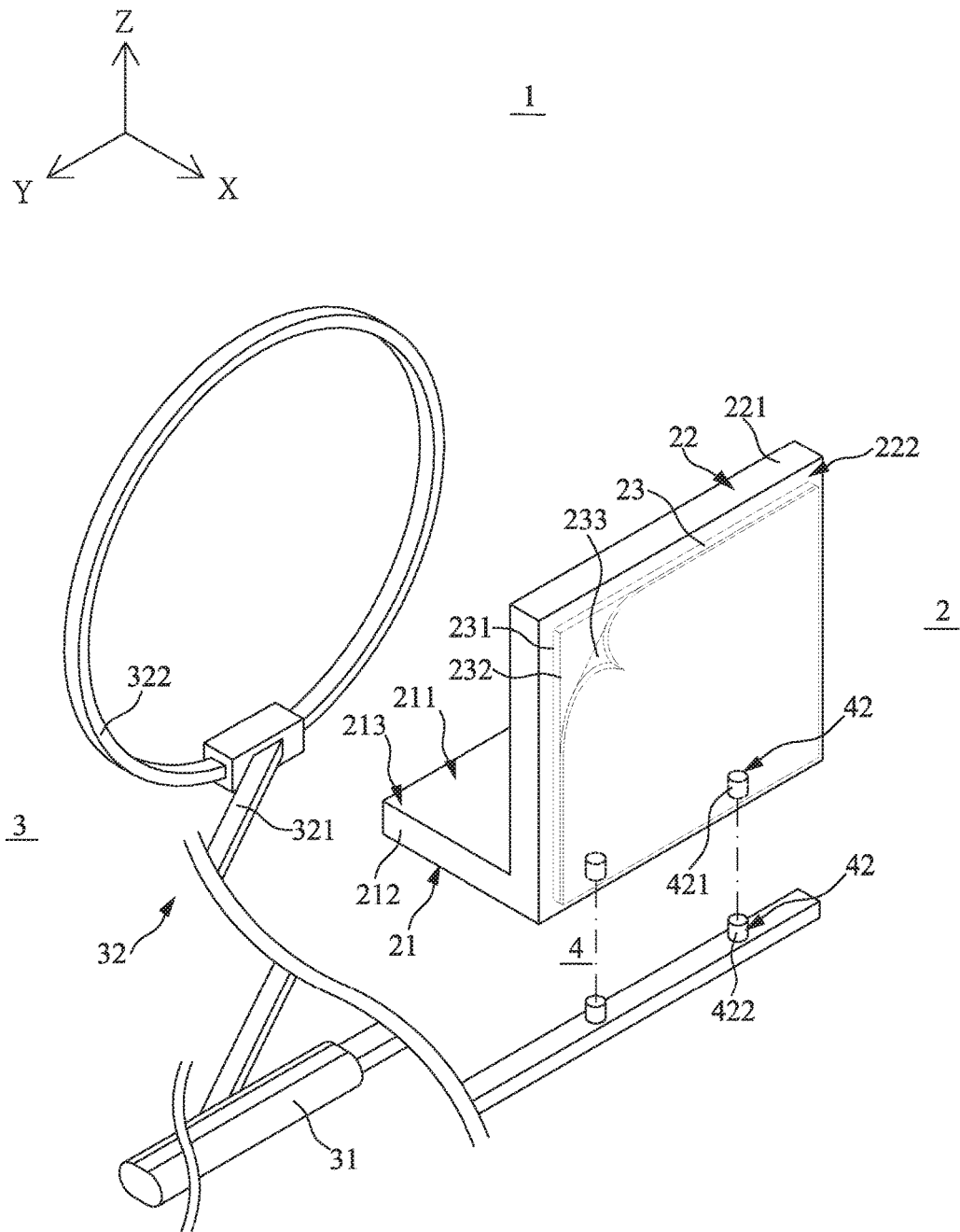
FIG. 9 is an exploded perspective view of a bite-block and film-holding device according to a third preferred embodiment of the present invention, showing a snap-fit structure thereof.

FIG. 9 shows a bite-block and film-holding device 1 according to a third preferred embodiment of the present invention. The third preferred embodiment is different from the first one in that the coupling structure 4 thereof for connecting the aiming assembly 3 to the disposable film holder 2 is configured as a snap-fit structure 42. The snap-fit structure 42 includes a plurality of sunken holes 421 provided on the film-holding portion 22 at a surface that correspondingly contacts with the coupling arm 31, and a plurality of bosses 422 provided on the coupling arm 31 at a surface that correspondingly contacts with the film-holding portion 22. It is understood the insertion hole 411 of the insert-to-connect structure 41 and the sunken holes 421 of the snap-fit structure 42 according to the present invention are not necessarily provided on the bite block portion 21 or on a location of the disposable film holder 2 joining the bite block portion 21 and the film-holding portion 22. It is doubtlessly the insertion hole 411 and the sunken holes 421 can be otherwise provided on the film-holding portion 22. Since the third preferred embodiment is similar to the first one in all other structural features, it is not repeatedly described herein.

Figure 10:
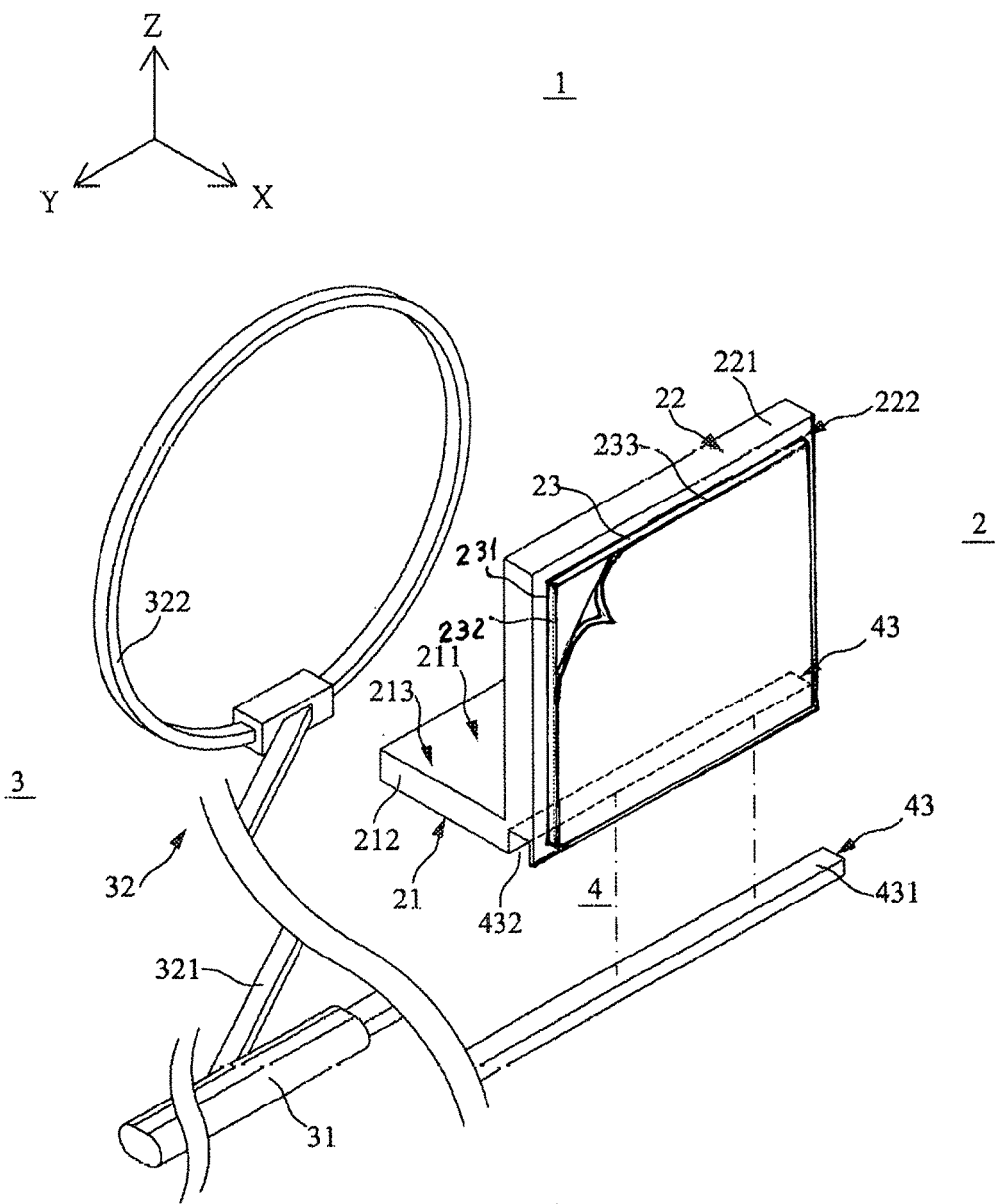
FIG. 10 is an exploded perspective view of a bite-block and film-holding device according to a fourth preferred embodiment of the present invention, showing an interference-fit structure thereof.

FIG. 10 shows a bite-block and film-holding device 1 according to a fourth preferred embodiment of the present invention. The fourth preferred embodiment is different from the first one in that the coupling structure 4 thereof for connecting the aiming assembly 3 to the disposal film holder 2 is configured as an interference-fit structure 43. The interference-fit structure 43 includes a rod 431 extended from an end of the coupling arm 31 and a groove 432 formed on the film-holding portion 22 for correspondingly receiving the rod 431 therein. When the rod 431 is fitted in the groove 432, the rod 431 and the bite block portion 21 are located in the same X-Y plane to form a co-planar state.

Figure 11:
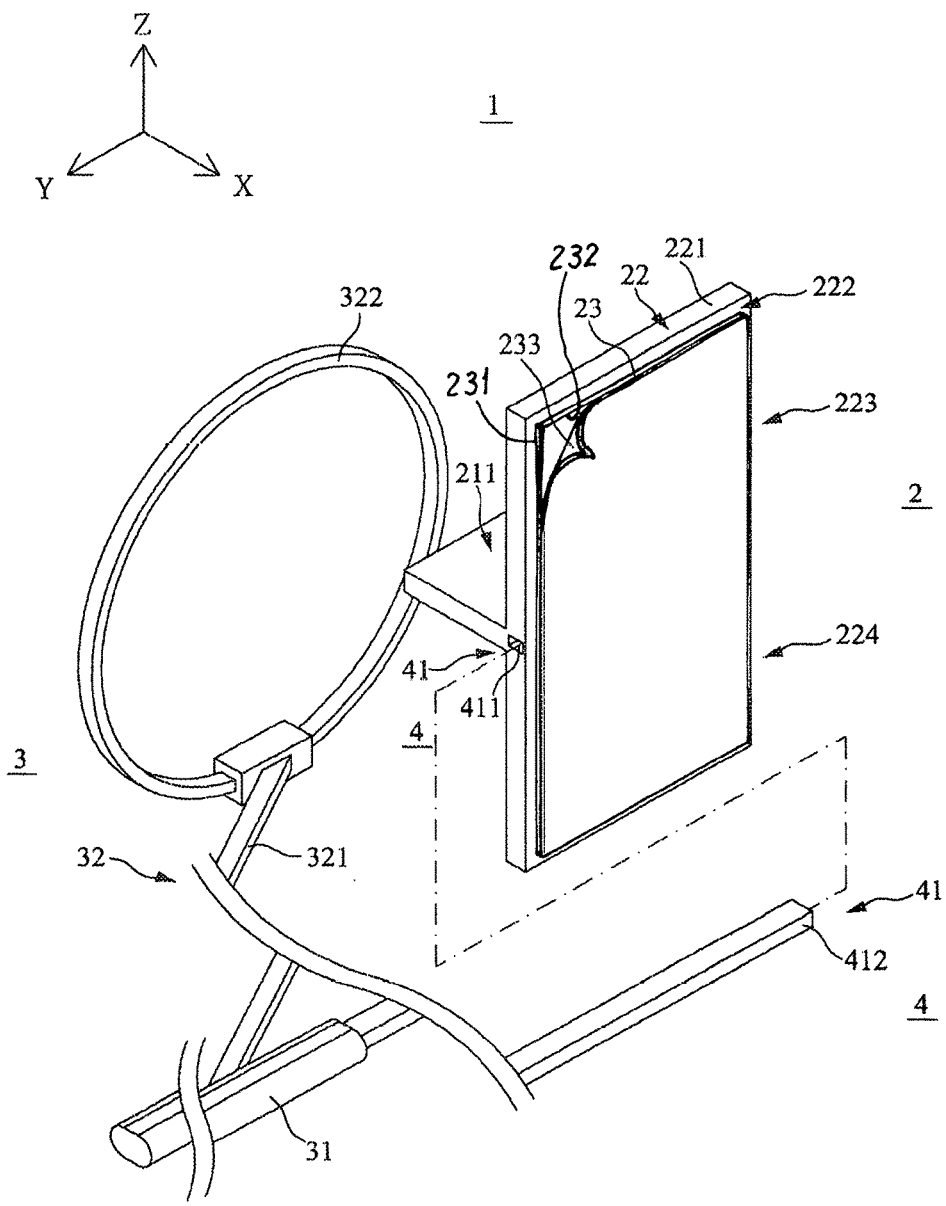
FIG. 11 is an exploded perspective view of a bite-block and film-holding device according to a fifth preferred embodiment of the present invention, showing an insert-to-connect structure thereof.

FIG. 11 shows a bite-block and film-holding device 1 according to a fifth preferred embodiment of the present invention. The fifth preferred embodiment is different from the first one in that the film-holding portion 22 thereof is extended upward and downward in the Y-Z plane relative to the bite block portion 21 to include an upper part 223 and a lower part 224. The upper part 223 is located corresponding to the patient's upper teeth 8, while the lower part 224 corresponding to the patient's lower teeth 9. Since the fifth preferred embodiment is similar to the first one in all other structural features, it is not repeatedly described herein.

Figure 12:
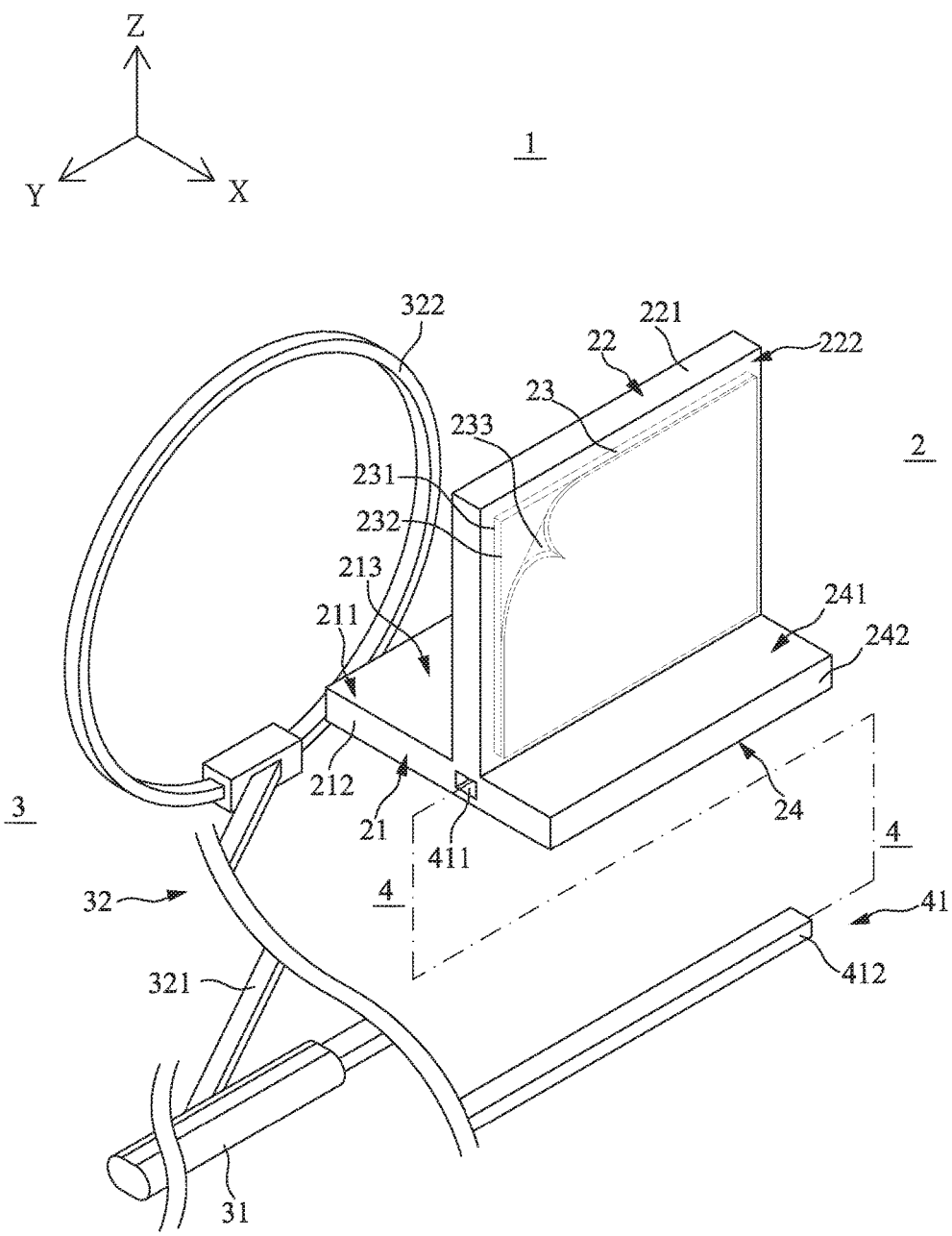
FIG. 12 is an exploded perspective view of a bite-block and film-holding device according to a sixth preferred embodiment of the present invention, showing an insert-to-connect structure thereof.

Please refer to FIG. 12 that shows a bite-block and film-holding device 1 according to a sixth preferred embodiment of the present invention. The sixth preferred embodiment is different from the first one in that it further includes an alignment portion 24, which is connected to the holding surface 222 of the film-holding portion 22 to extend in an X-Y plane and form a supporting surface 241. The x-ray film 5 or the digital image sensor 6 is adhered to the film-holding portion 22 with an edge in contact with the supporting surface 241. In this manner, the x-ray film 5 or the digital image sensor 6 can be held to the disposable film holder 2 stably and accurately. In the illustrated sixth preferred embodiment, the alignment portion 24 is formed of one single alignment member 242. The alignment member 242 extends from the holding surface 222 of the film-holding portion 22 in an X-Y plane. In this case, the bite block portion 21 and the alignment portion 24 are located at two opposite sides of the film-holding portion 22.

In the illustrated sixth preferred embodiment, the supporting surface 241 of the alignment portion 24 extends in the X-Y plane by a distance shorter than the distance by which the bite surface 211 of the bite block portion 21 extends in the X-Y plane. According to a preferred embodiment, the supporting surface 241 extends in the X-Y plane by a distance smaller than or equal to 8 mm (8 mm). This is because most of the currently available digital image sensors 6 for dental radiographic examination have a thickness not exceeding 8 mm. Meanwhile, the bite surface 211 is set to extend in the X-Y plane by a distance larger than or equal to the extending distance of the supporting surface 241. Since the sixth preferred embodiment is similar to the first one in all other structural features, it is not repeatedly described herein.

Figure 13:
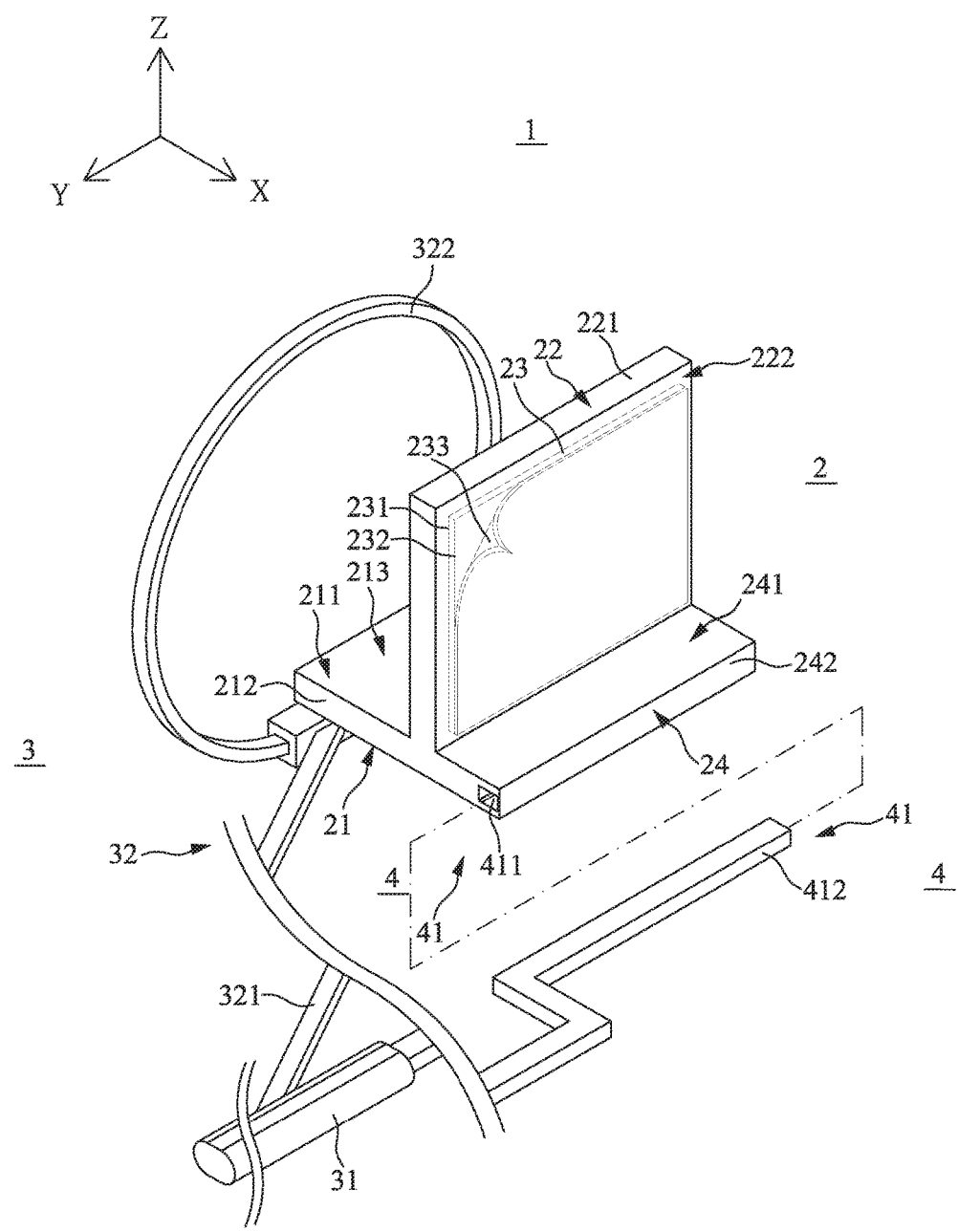
FIG. 13 is an exploded perspective view of a bite-block and film-holding device according to a seventh preferred embodiment of the present invention, showing an insert-to-connect structure thereof.

FIG. 13 shows a bite-block and film-holding device 1 according to a seventh preferred embodiment of the present invention. The seventh preferred embodiment is different from the sixth one in that the insert-to-connect structure 41 on the coupling arm 31 of the aiming assembly 3 is correspondingly connected to the alignment portion 24. In the illustrated seventh preferred embodiment, the insert-to-connect structure 41 includes an insertion hole 411 provided on the alignment portion 24 and an insertion rod 412 provided on the coupling arm 31 for correspondingly inserting into the insertion hole 411. By inserting the insertion rod 412 into the insertion hole 411, the aiming assembly 3 is coupled to the disposable film holder 2. Further, the coupling arm 31 in the seventh preferred embodiment is configured as a bent bar. When a front end of the coupling arm 31, i.e. the insertion rod 412, is inserted into the insertion hole 411, a bent section of the coupling arm 31 that is immediately located outside the bite block portion 21 now fitly bears against one side of the bite block portion 21 to locate in the same X-Y plane as the bite block portion 21. Since the seventh preferred embodiment is similar to the sixth one in all other structural features, it is not repeatedly described herein.

Figure 14:
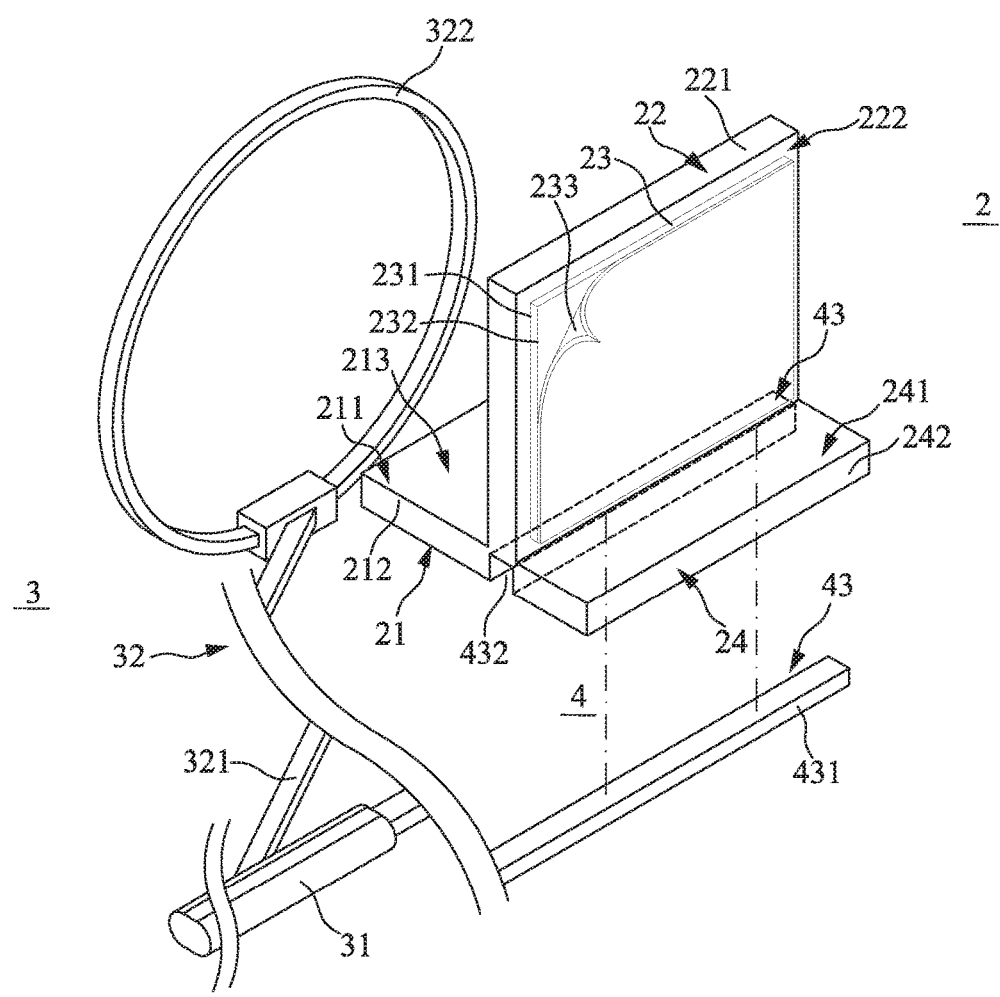
FIG. 14 is an exploded perspective view of a bite-block and film-holding device according to an eighth preferred embodiment of the present invention, showing an interference-fit structure thereof.

FIG. 14 shows a bite-block and film-holding device 1 according to an eighth preferred embodiment of the present invention. The eighth preferred embodiment is different from the sixth one in that the coupling structure 4 thereof for connecting the aiming assembly 3 to the disposal film holder 2 is configured as an interference-fit structure 43. The interference-fit structure 43 includes a rod 431 extended from an end of the coupling arm 31 and a groove 432 formed on the film-holding portion 22 for correspondingly receiving the rod 431 therein. When the rod 431 is fitted in the groove 432, the rod 431 and the bite block portion 21 are located in the same X-Y plane to form a co-planar state.

Figure 15:
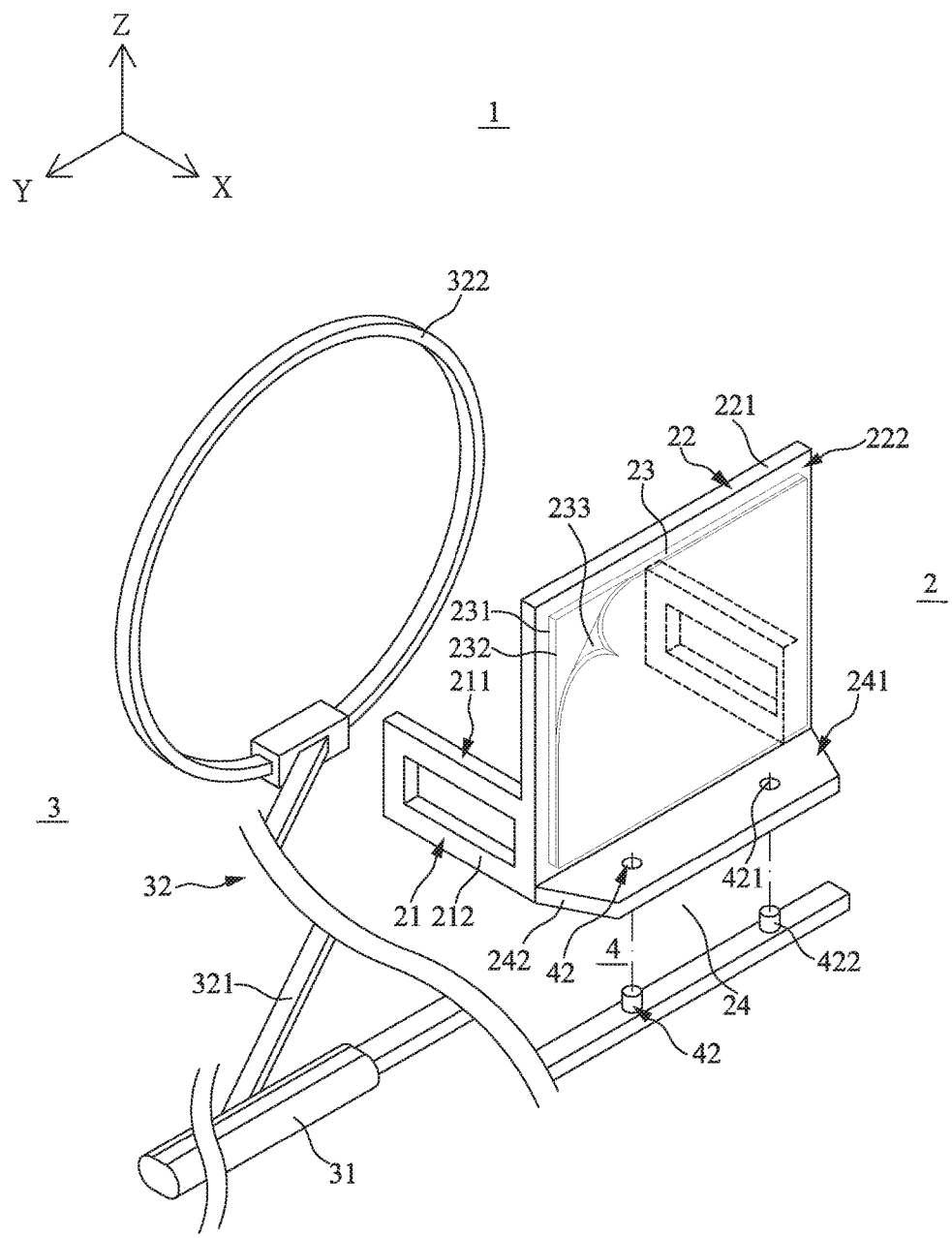
FIG. 15 is an exploded perspective view of a bite-block and film-holding device according to a ninth preferred embodiment of the present invention, showing a snap-fit structure thereof.

FIG. 15 shows a bite-block and film-holding device 1 according to a ninth preferred embodiment of the present invention. The ninth preferred embodiment is different from the sixth one in that the bite block portion 21 thereof is formed of two spaced brackets, which are fixedly connected to two lateral ends on the same side of the film-holding portion 22 to extend in two spaced Y-Z planes. Each of the brackets includes a set of corresponding upper arm and lower arm, and a supporting post connected to between the upper and low arms. The upper arms of the two brackets together define an upper bite surface, while the lower arms of the two brackets together define a lower bite surface. In the process of dental radiographic imaging, the patient bites on the bite block portion 21 with upper teeth 8 contacting with the upper bite surface defined by the upper arms and the lower teeth 9 contacting with the lower bite surface defined by the lower arms.

Further, in the ninth preferred embodiment, the coupling structure 4 thereof for connecting the aiming assembly 3 to the disposable film holder 2 is configured as a snap-fit structure 42. The snap-fit structure 42 includes a plurality of sunken holes 421 provided on the alignment portion 24 and a plurality of bosses 422 provided on the coupling arm 31 corresponding to the sunken holes 421. In the illustrated ninth preferred embodiment, the supporting surface 241 extends from the holding surface 222 of the film-holding portion 22 in the X-Y plane with a forwardly gradually reduced width. Since the ninth preferred embodiment is similar to the sixth one in all other structural features, it is not repeatedly described herein.

Figure 16:
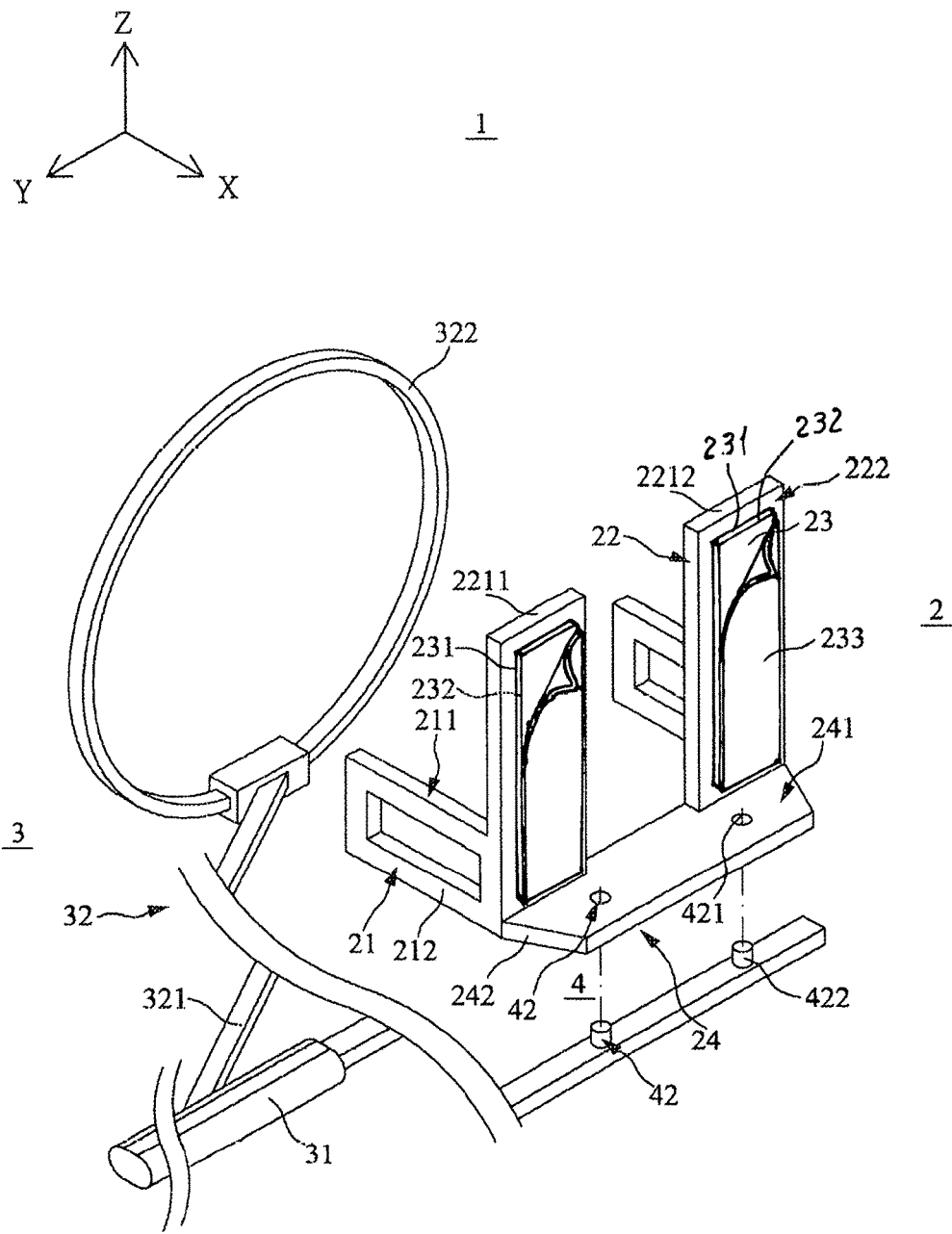
FIG. 16 is an exploded perspective view of a bite-block and film-holding device according to a tenth preferred embodiment of the present invention, showing a snap-fit structure thereof.

FIG. 16 shows a bite-block and film-holding device 1 according to a tenth preferred embodiment of the present invention. The tenth preferred embodiment is different from the ninth one in that the film-holding portion 22 thereof is formed of a first film-holding member 2211 and a second film-holding member 2212, which are laterally spaced from each other. Outer surfaces of the first and second film-holding members 2211, 2212 are located in the same Y-Z plane to together define the holding surface 222. The spaced first and second film-holding members 2211, 2212 are located corresponding to the two brackets of the bite block portion 21. Since the tenth preferred embodiment is similar to the ninth one in all other structural features, it is not repeatedly described herein.

With the above arrangements, the bite-block and film-holding device 1 of the present invention has the advantages of small volume, low manufacturing cost and simple structural design. With the bonding member 23, the film-holding portion 22 of the disposable film holder 2 according to the present invention can be used to hold x-ray films 5 or digital image sensors 6 that are produced by different manufacturers and have different specifications. During the process of dental radiographic imaging, the patient bites the bite block portion 21 between teeth with the x-ray film 5 or the digital image sensor 6 located corresponding to the patient's teeth that require dental radiographic imaging. After completion of the dental radiographic imaging, the x-ray film 5 or the digital image sensor 6 is removed from the disposable film holder 2 and can be disinfected for reuse. The entire disposable film holder 2, which has the patient's saliva and other oral cavity tissues attached thereto, is discarded along with the coupling arm 31 of the aiming assembly 3. In this way, it is able to ensure the sanitation and safety of tools used in dental examination.

In the process of dental radiographic imaging, the aiming assembly 3 is located outside the patient's oral cavity and can be precisely aligned with the disposable film holder 2 that is located inside the patient's oral cavity. The dental radiographic imaging assistant can efficiently position the disposable film holder 2 in the patient's mouth without the need of touching any part of the disposable film holder 2 or asking the patient to hold the x-ray film 5 or the digital image sensor 6 with fingers. In this manner, it is able to avoid the invasion of dirt or bacteria into the patient's mouth via the dental radiographic imaging assistant's or the patient's fingers. Via the aiming assembly 3 located outside the patient's oral cavity, the dental radiographic imaging assistant is able to accurately align the camera device 7 with the teeth to be examined. The aiming assembly 3 not only largely shortens the time needed for the dental radiographic imaging, but also reduces the number of times the x-ray film 5 or the digital image sensor 6 is used. Therefore, the service life of the x-ray film 5 or the digital image sensor 6 can be extended.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A bite-block and film-holding device being configured for use with any one of an x-ray film and a digital image sensor and held by a patient between teeth to align with an external camera device for dental radiographic imaging of the patient's teeth, comprising:
   a disposable film-holder including:
   a bite block portion having two bite surfaces respectively extended in an X-Y plane;
   a film-holding portion made of a plastic material and connected to an end of the bite block portion, and having a holding surface extended in a Y-Z plane; and
   a bonding member having two bonding surfaces provided on two opposite sides thereof; one of the bonding surfaces being adhered to the holding surface of the film-holding portion while the other bonding surface is used to adhesively hold the x-ray film or the digital image sensor thereto; and
   an aiming assembly including:
   a coupling arm having an end coupled to the disposable film holder;
   an aiming ring assembly installed on the camera device and connected to another end of the coupling arm; and the aiming ring assembly being adjustable in position for the camera device to face at right angle to the holding surface of the film-holding portion; and
   an alignment portion for ensuring accurate holding of the x-ray film or the digital image sensor to the film-holding portion; the alignment portion being connected to the holding surface of the film-holding portion to provide a supporting surface extended in an X-Y plane; and the x-ray film or the digital image sensor being adhered to the film-holding portion with an edge in contact with the supporting surface;
   wherein, after completion of the dental radiographic imaging of the patient's teeth, the disposable film holder is separated from the aiming assembly and another new disposable film holder is coupled to the aiming assembly for use in the dental radiographic imaging of another patient.

2. The bite-block and film-holding device as claimed in claim 1, wherein the bite block portion is formed of one single bite member, of which an upper and a lower side form an upper bite surface and lower bite surface, respectively.

3. The bite-block and film-holding device as claimed in claim 1, wherein the film-holding portion is formed of one single film-holding member; the film-holding member including an upper part and a lower part, which are extended upward and downward in the Y-Z plane relative to the bite block portion; the upper part being located corresponding to the patient's upper teeth, and the lower part being located corresponding to the patient's lower teeth.

4. The bite-block and film-holding device as claimed in claim 1, wherein the bonding member further includes a release layer attached to one of the bonding surfaces that is to be adhered to the x-ray film or the digital image sensor.

5. The bite-block and film-holding device as claimed in claim 1, wherein the alignment portion is formed of one single alignment member; the alignment member extending from the holding surface of the film-holding portion in an X-Y plane; and the bite block portion and the alignment portion being located at two opposite sides of the film-holding portion.

6. The bite-block and film-holding device as claimed in claim 1, wherein the aiming ring assembly includes a sub-coupling arm connected at an end to the coupling arm and an aiming ring connected to another opposite end of the sub-coupling arm.

7. The bite-block and film-holding device as claimed in claim 6, wherein the coupling arm and the sub-coupling arm are respectively configured as a shaft and a sleeve; and the shaft being connected to the sleeve by correspondingly fitting the shaft in the sleeve.

8. The bite-block and film-holding device as claimed in claim 1, wherein the coupling arm is connected to one of the bite block portion, the film-holding portion and the alignment portion via a coupling structure.

9. The bite-block and film-holding device as claimed in claim 8, wherein the coupling structure is configured as an insert-to-connect structure, which includes an insertion hole provided on one of the bite block portion, the film-holding portion and the alignment portion and an insertion rod provided on the coupling arm for correspondingly inserting into the insertion hole.

10. The bite-block and film-holding device as claimed in claim 8, wherein the coupling structure is configured as a snap-fit structure, which includes a plurality of sunken holes provided on one of the bite block portion, the film-holding portion and the alignment portion at a surface that correspondingly contacts with the coupling arm, and a plurality of bosses provided on the coupling arm at a surface that correspondingly contacts with one of the bite block portion, the film-holding portion and the alignment portion.

11. The bite-block and film-holding device as claimed in claim 8, wherein the coupling structure is configured as an interference-fit structure, which includes a rod extended from an end of the coupling arm and a groove formed on one of the bite block portion, the film-holding portion and the alignment portion for correspondingly receiving the rod therein; and the rod fitted in the groove being coplanar with the bite block portion, the film-holding portion and the alignment portion.

* * * * *